(12) United States Patent
McKinnon

(10) Patent No.: US 10,232,140 B2
(45) Date of Patent: Mar. 19, 2019

(54) ANTI-OCCLUSION CATHETER ADAPTER

(75) Inventor: Austin Jason McKinnon, Herriman, UT (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 981 days.

(21) Appl. No.: 11/959,295

(22) Filed: Dec. 18, 2007

(65) Prior Publication Data
US 2009/0157007 A1    Jun. 18, 2009

(51) Int. Cl.
*A61M 25/00*    (2006.01)
*A61M 39/10*    (2006.01)

(52) U.S. Cl.
CPC .... *A61M 25/0014* (2013.01); *A61M 25/0097* (2013.01); *A61M 39/10* (2013.01)

(58) Field of Classification Search
CPC .. A61M 25/0014; Y10S 128/06; Y10S 128/26
USPC ........................................................ 604/533
See application file for complete search history.

(56) References Cited

U.S. PATENT DOCUMENTS

| | | | |
|---|---|---|---|
| 3,633,579 A * | 1/1972 | Alley et al. ................... | 604/508 |
| 3,921,631 A * | 11/1975 | Thompson .......... | A61M 25/065 604/160 |
| 4,000,739 A * | 1/1977 | Stevens ................ | A61M 25/00 600/433 |
| 4,256,106 A * | 3/1981 | Shoor ................... | A61M 39/14 251/149.1 |
| 4,445,893 A * | 5/1984 | Bodicky ........... | A61M 25/0606 604/165.04 |
| 4,626,245 A * | 12/1986 | Weinstein ......... | A61M 39/0606 137/849 |
| 4,723,948 A | 2/1988 | Clark et al. | |
| 4,781,703 A * | 11/1988 | Walker et al. ................ | 604/264 |
| 4,846,812 A * | 7/1989 | Walker et al. ................ | 604/264 |
| 4,880,414 A | 11/1989 | Whipple | |
| 4,909,798 A * | 3/1990 | Fleischhacker ... | A61M 39/0606 137/846 |
| 5,149,330 A * | 9/1992 | Brightbill ..................... | 604/523 |
| 5,167,647 A | 12/1992 | Wijkamp et al. | |
| 5,226,898 A | 7/1993 | Gross | |
| 5,256,145 A | 10/1993 | Atkinson et al. | |
| 5,330,449 A * | 7/1994 | Prichard et al. .............. | 604/533 |

(Continued)

FOREIGN PATENT DOCUMENTS

| | | |
|---|---|---|
| EP | 0 616 817 A1 | 9/1994 |
| JP | 6-210003 | 8/1994 |
| WO | WO 99/16498 A1 | 4/1999 |

*Primary Examiner* — Bhisma Mehta
*Assistant Examiner* — Matthew A Engel
(74) *Attorney, Agent, or Firm* — Kirton & McConkie; Craig Metcalf; Kevin Stinger

(57) ABSTRACT

A support device for preventing an occlusion of a catheter's root region including an extended, flexible member extending from an end of a catheter adapter. The flexible extension is tapered such that additional support is provided to the portions of the root region most susceptible to an occlusion. Additionally, the flexible extension provides shielding to the root region thereby preventing contamination of the same. Finally, the flexible extension provides a marking function whereby the technician may insert the catheter tube until such a point that the flexible extension contacts the patient thereby preventing over insertion of the catheter tube.

11 Claims, 4 Drawing Sheets

(56) References Cited

U.S. PATENT DOCUMENTS

| | | | | |
|---|---|---|---|---|
| 5,380,301 A | * | 1/1995 | Prichard | A61M 25/0014 604/533 |
| 5,651,776 A | * | 7/1997 | Appling | A61M 39/10 285/332 |
| 5,830,196 A | | 11/1998 | Hicks | |
| 5,830,401 A | | 11/1998 | Prichard et al. | |
| 6,068,622 A | * | 5/2000 | Sater et al. | 604/524 |
| 6,074,379 A | | 6/2000 | Prichard | |
| 6,228,073 B1 | | 5/2001 | Noone et al. | |
| 6,273,404 B1 | | 8/2001 | Holman et al. | |
| 6,332,874 B1 | * | 12/2001 | Eliasen et al. | 604/174 |
| 6,575,959 B1 | * | 6/2003 | Sarge | A61M 25/0009 128/DIG. 26 |
| 6,595,958 B1 | * | 7/2003 | Mickley | 604/164.01 |
| 7,407,498 B2 | * | 8/2008 | Olson | 604/534 |
| 7,594,911 B2 | * | 9/2009 | Powers et al. | 604/533 |
| 2001/0049519 A1 | * | 12/2001 | Holman et al. | 604/534 |
| 2005/0209583 A1 | * | 9/2005 | Powers | A61M 25/0014 604/533 |
| 2005/0251102 A1 | * | 11/2005 | Hegland et al. | 604/500 |
| 2009/0264866 A1 | * | 10/2009 | Powell | 604/533 |
| 2010/0100074 A1 | * | 4/2010 | Smith et al. | 604/533 |

* cited by examiner

ANTI-OCCLUSION CATHETER ADAPTER

BACKGROUND OF THE INVENTION

The present disclosure relates generally to infusion therapy with vascular access devices, and relates specifically to infusion therapy with intravenous catheters. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Intravenous therapy is facilitated by vascular access devices located outside the vascular system of a patient (extravascular devices). Extravascular devices that may access a patient's peripheral or central vasculature, either directly or indirectly include closed access devices, such as the BD Q-SYTE closed Luer access device of Becton, Dickinson and Company, syringes, split access devices, catheters, and intravenous (IV) fluid chambers. A vascular device may be indwelling for short term (days), moderate term (weeks), or long term (months to years). A vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter is commonly incorporated into a catheter adapter to aid in the ease of use, accessibility and utility of the catheter. A catheter adapter is generally a rigid, plastic, tubular member adapted to house one end of the catheter such that one end of the catheter is supported by the catheter adapter, the body and tip of the catheter extending beyond a first end of the catheter adapter. The catheter adapter generally further comprises a second end adapted to receive additional infusion components for use with the catheter. For example, the second end of a catheter adapter may include a set of threads for attaching an intravenous line or for coupling a syringe to the catheter adapter thereby providing access to the patient via the attached catheter.

The catheter may be inserted transcutaneously or may be surgically implanted beneath the patient's skin. When inserted transcutaneously, the insertion of the catheter is commonly aided by a hypodermic needle. The hypodermic needle is commonly housed inside the lumen of the catheter such that the gauge of the needle approximates the inner diameter of the catheter. The needle is positioned within the catheter such that the needle tip extends beyond the tip of the catheter whereby the needle is used to penetrate the patient's vein and provide an opening for insertion of the catheter.

The needle and catheter generally approach the patient's vein at an angle of about 30° wherein the needle initially punctures the patient's skin and then continues into the vein. Once the needle and catheter tip enter the patient's vein, the needle and catheter are then repositioned so that the needle and catheter are brought into a position generally parallel with the patient's vein so that the needle and catheter may be inserted into the lumen of the patient's vein. When the catheter has been properly positioned within the patient's vein, the needle is removed from the lumen of the catheter and the catheter adapter is secured to the patient to prevent premature removal of the catheter.

Typically the catheter adapter is secured to the patient by fastening the catheter adapter to the patient's skin via tape and/or steri-strips. In securing the catheter adapter to the patient's skin, the root region of the catheter must arch to accommodate the catheter's transition from the generally parallel, secured orientation of the catheter adapter, to the insertion angle of the catheter, an angle of approximately 30°. General practice requires that the catheter be inserted into a patient such that an extended section of catheter is left between the patient and the catheter adapter to allow for transitional arching of the catheter.

Several issues exist regarding the need for this exposed, archable length of catheter. First, in making this arch, the catheter is biased towards the patient's skin and thus the root region of the catheter experiences leverage forces wherein the catheter acts as a lever and the first end of the catheter adapter acts as a fulcrum exerting an upward force on the root region of the catheter. This upward force of the first end of the catheter adapter is undesirable due to the likelihood of occlusion of the root region of the catheter against the more rigid catheter adapter. Occlusion typically occurs as the patient and or the catheter is moved thereby increasing the angle of insertion in relation to the fixed position of the catheter adapter. For example, if the repositioning of the catheter and/or patient inserts the catheter further into the patient, the archable length of catheter between the patient and the catheter adapter is decreased thereby increasing the angle of insertion and the upward force of the immobilized catheter adapter on the root region of the catheter. As the angle of insertion increases the upward force of the catheter adapter also increases until such point that the structural rigidity of the catheter is overcome and the catheter kinks in order to continue accommodating the catheter's transition from the catheter adapter into the patient.

Occlusion of the catheter is undesirable as occlusions serve to slow or stop the flow through the catheter thereby creating undesirable backpressures that may cause the infusion system to malfunction and/or be damaged. Additionally, occlusions reduce the efficiency of the infusion system which could effect the treatment and/or diagnosis of the patient.

Second, due to the exposed nature of the arched catheter section, the exposed catheter section may become contaminated and pose a health risk to the patient. For example, an exposed section of catheter may become contaminated and then be inserted into the patient as the patient and/or catheter is readjusted due to normal use by the patient and/or technician. To reduce the likelihood of contamination and subsequent exposure to the patient, technicians seek to minimize the length of exposed catheter by initially over-inserting the catheter into the patient. In reducing the length of exposed catheter, the upward force of the first end of the catheter adapter is increased thereby increasing the likelihood of occlusion within the root region of the catheter.

Contamination of the catheter and/or patient is undesirable for obvious reasons. For example, contamination may lead to secondary infection and/or complications unanticipated by the treating physician. Furthermore, a contaminated catheter may introduce a virus and/or bacteria to the patient that may conflict with the patient's primary therapy such that the patient is unable to receive further needed treatment.

Therefore, a need exists for systems and methods that reduce occlusions at the root region of the catheter, prevent over-insertion of the catheter and prevent contamination of the same.

BRIEF SUMMARY OF THE INVENTION

The anti-occlusion catheter adapter according to the invention overcome the problems of the prior art by providing additional support to the root region of the catheter thereby buttressing the catheter root and preventing occlusion of the catheter within this occlusion-prone region. Additionally, the additional support provides a sheath that protects the root region from contamination and prevents over-insertion.

The anti-occlusion catheter adapter of the present invention includes a catheter tube wherein the catheter tube is attached to a catheter adapter to aid in the placement and the support of the catheter in a patient's vascular system. In one embodiment, the catheter tube may include a variety of materials including silicone, IntiSilf silicone, polyurethane, and polyethylene. In another embodiment, the catheter tube may also include a rounded tip or a tip with square corners. In a specific embodiment, the catheter tube is silicone and includes a rounded tip. The catheter tube has an inner diameter and an outer diameter, each of which may be selected based on the needs of the user. For example, in one embodiment the inner diameter is selected to accommodate a specific gauge of needle such that the needle may be slidably housed within the catheter.

The catheter tube material may also be impregnated or striated with an additional material for added resistance of occlusions and/or to provide a function, such as to add the function of radiological detection via a radiopaque material. In one specific embodiment, the catheter tube is striated with barium sulfate thereby providing radiological detection of the catheter tube within the patient. In another specific embodiment, the material of the catheter tube is impregnated with barium sulfate in a spiral formation such that the impregnated material provides additional strength to the catheter tube to prevent occlusion of the catheter, as well as provides for radiological detection of the catheter tube within the patient.

The catheter tube is attached to a first end of a catheter adapter such that the catheter tube and the catheter adapter comprise a single unit. The catheter tube may be attached to the catheter adapter using a variety of methods including heated tool, hot gas, vibration, spin, ultrasonic, induction, radio frequency, microwave, resistance, extrusion, electrofusion, infrared, laser welding, mechanical fastening, and/or chemical bonding. In one embodiment, the catheter tube is attached to the catheter adapter via a mechanical fastener wherein the catheter tube is inserted into the catheter adapter and a tubing insert is inserted into the end of the catheter tube such that a fluidtight attachment is formed. The catheter adapter may include a variety of materials including polypropylene, polyvinyl chloride, and/or polyethylene. In one specific embodiment, the catheter adapter is polypropylene.

The catheter adapter is generally cylindrical with an opening at a second end, the second end being opposite to the first end of the catheter adapter, the first end comprising an opening through with the catheter tube extends. The catheter adapter may include structural features to accommodate use of the catheter adapter in an infusion system. For example, in one embodiment the second end of the catheter adapter includes a set of threads for compatibly receiving an adapter, such as a male Luer, for attaching the catheter adapter to an infusion system. In another embodiment, the exterior of the catheter adapter includes a set of annular ridges wherein the annular ridges are a molded feature of the catheter adapter to aid in gripping and/or controlling the catheter adapter.

The first end of the catheter adapter may also include a feature to support the root region of the catheter. For example, in one embodiment the first end of the catheter adapter is extended in a tapered manner such that the first end of the catheter adapter forms a flexible buttress surrounding the root region of the catheter tube. This flexible buttress may comprise the same material as the catheter adapter and may be attached to the first end of the catheter adapter or may be molded as part of the catheter adapter.

In one embodiment, the injection mold for the catheter adapter is designed such that a controlled amount of flash is permitted to extend beyond first end of the catheter adapter along the inserted molding pin such that the first end of the catheter adapter is extended. This controlled amount of flash results in a thin, tapered and flexible extension of the first end of the catheter adapter.

In another embodiment, the injection mold for the catheter adapter is designed to include an extension of material extending outward from the first end of the catheter adapter thereby producing a molded, flexible extension. In both embodiments, the inner profile of the flexible extension approximates the outer profile of the catheter tube such that a small air gap is created between the outer surface of the catheter tube and the inner surface of the flexible extension. This air gap permits the catheter tube to move independently of the flexible extension.

The flexible extension is generally tubular as defined by an inner surface, an outer surface and a length, the length being defined as the distance between the proximal end and the distal end of the flexible extension. The thickness between the inner surface and the outer surface varies along the length such that flexible extension is tapered. For example, the proximal end of the flexible extension is attached to the first end of the catheter adapter and extends longitudinally out of the first end of the catheter adapter terminating at a distal end. In one embodiment the proximal end of the flexible extension has a thickness greater than the thickness of the distal end.

As previously discussed, the inner surface of the flexible extension approximates the outer profile of the catheter tube. As such the profile of the inner surface of flexible extension is generally linear while the profile of the outer surface of the flexible extension is generally ramped. The ramped profile of the outer surface of the flexible extension is such that the outer diameter of the proximal end of the flexible extension is greater than outer diameter of the distal end of the flexible extension. The ramped design of the flexible extension provides an inverse relationship between the thickness of the flexible extension and the flexibility of the flexible extension. For example, the thicker proximal end is less flexible than the thinner distal end while the middle portion of the flexible extension is less flexible than the distal end but more flexible than the proximal end.

The buttressing effect of the flexible extension is realized following the insertion of the catheter tube into a patient. The catheter tube is inserted into a patient via the assistance of a needle. In one embodiment, the needle is a hypodermic needle and the needle is inserted through the interior of the catheter tube via the catheter adapter. In this same embodiment, the needle tip extends beyond the tip of the catheter tube such that the needle may penetrate the patient in order to introduce the catheter tube into the patient's vascular system. After the catheter tube has been placed within the patient's vascular system, the needle is removed and the catheter adapter is secured to the patient thereby ensuring that the catheter tube is not prematurely removed. In one embodiment the catheter adapter is secured to the patient via adhesive strips. The catheter adapter is secured following a parallel alignment of the catheter adapter with the patient's outer surface. This act of aligning the catheter adapter changes the angle of the catheter adapter in relation to the catheter tube such that the root region of the catheter tube is required to arch in order to accommodate the catheter adapter's new angle. At this point, the flexible extension contours to the root region's arch whereby the flexible extension provide support to the root region of the catheter tube thereby preventing an occlusion of the catheter tube at the root region.

The proximal end of the root region is that part of the root region that abuts the first end of the catheter adapter or that part of the root region that is covered by the proximal end of the flexible extension. The distal end of the root region is the part of the root region that is covered by the distal end of the flexible extension. The ramped feature of the flexible extension provide more rigid support (i.e. less flexible) at the proximal end of the root region and less rigid support (i.e. more flexible) at the distal end of the root region. This feature is important due to the increased likelihood of occlusion at the proximal end of the root region due to the abutting first end of the catheter adapter which serves as a fulcrum to kink the catheter tube. The ramped feature of the flexible extension serves to gradually reduce the overall leverage through the root region thereby reducing the fulcrum effect of the first end of the catheter adapter and preventing an occlusion within the root region.

The flexible extension also provides shielding to the root region of the catheter. When the catheter is inserted into the patient, the remaining, uninserted portion of the catheter is covered by the flexible extension such that the distal end of the flexible extension is in contact with the patient's skin thereby reducing the exposure of the root region to possible contamination. Additionally, the distal end of the flexible extension serves a marker function such that a technician may insert the catheter until such a position that the distal end of the flexible member contacts the patient, at which point the technician stops the insertion of the catheter. In this position, an optimal length of catheter is left uninserted thereby insuring that a proper transitional arch is formed with minimal likelihood of occlusion. Furthermore, the flexible extension prevents the catheter from further insertion thereby maintaining the correct angle of insertion for the catheter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
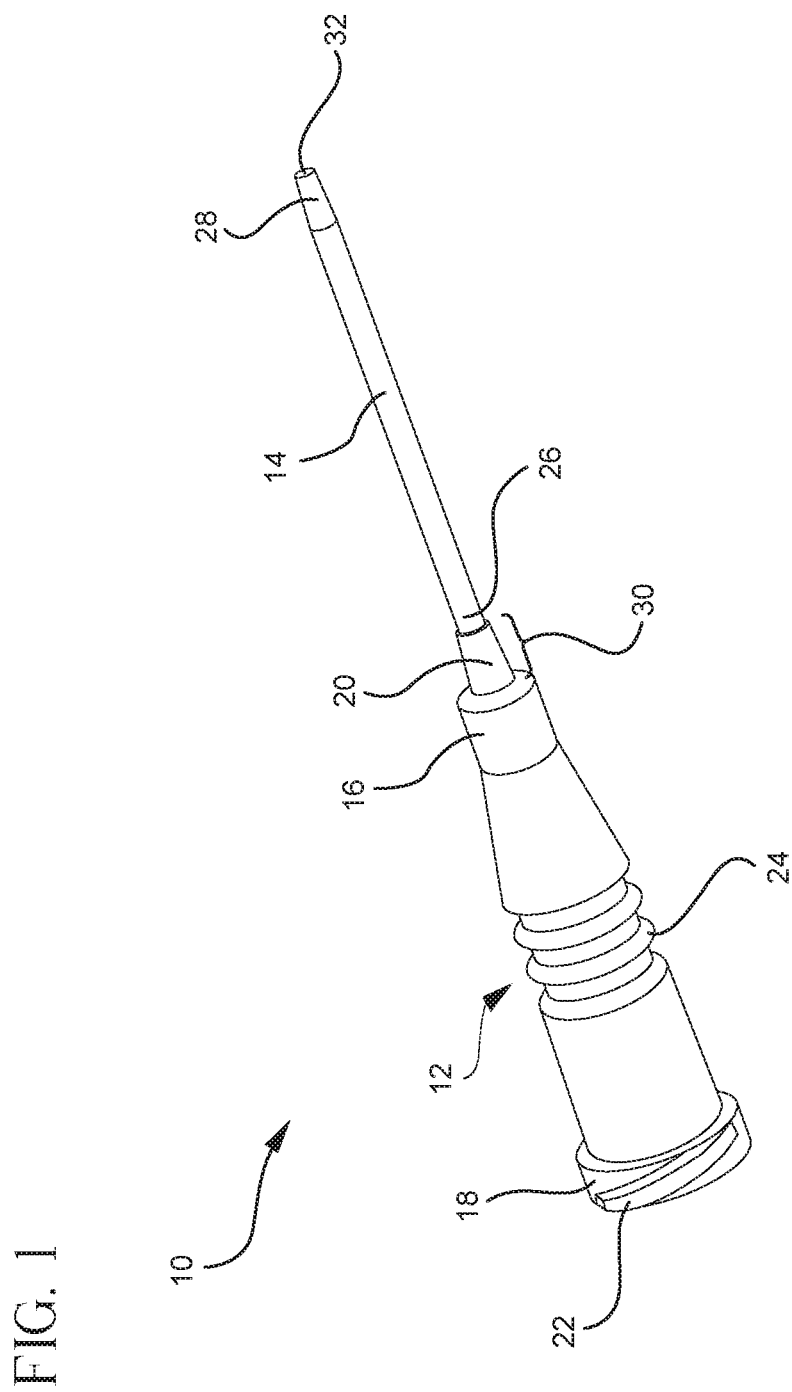
FIG. 1 is a perspective view of a catheter assembly including a catheter adapter with an extended first end comprising the flexible extension support device.

Referring now to FIG. 1, a catheter assembly 10 is illustrated comprising a catheter adapter 12 and a catheter tube 14. The catheter adapter 12 is generally cylindrical with a first end 16 and a second end 18, where the first end 16 is attached to a flexible extension 20, and the second end 18 may be attached to an infusion system (not shown). First end 16 has a generally cylindrical shape which forms a generally circular distal surface 16a. The catheter tube 14 is attached to the catheter adapter 12 in a fluidtight manner whereby a fluid may be transferred from the catheter adapter 12 into the catheter tube 14 for purposes of administering the liquid via the catheter assembly 10. The catheter tube 14 is generally cylindrical with a proximal end 26 and a distal end 28 wherein the proximal end 26 comprises a root region 30, and the distal end 28 comprises a catheter tip 32. The catheter tip 32 is tapered such that the outer diameter of the catheter tip 32 converges on the opening of the distal end 28 of the catheter tube 14 thereby providing easier introduction of the catheter into the patient's vascular system.

The second end 18 of the catheter adapter 12 also comprises an attachment adapter 22 whereby the catheter assembly 10 is capable of attaching to an infusion system (not shown). The attachment adapter 22 may include a set of male threads for receiving a compatible set of female threads whereby a fluidtight connection is made. The second end 18 of the catheter adapter 12 is also sufficiently open such that a needle assembly and/or male Luer may be attached to the catheter adapter 12 in a fluidtight manner. The attachment adapter 22 may also be utilized to attach a needle assembly or a male Luer as needed.

The catheter adapter 12 may also include a gripping feature 24 to aid in the handling and securing of the catheter assembly 10. The gripping feature 24 may include a set of molded, annular rings positioned so as to provide an optimal gripping surface. The gripping feature 24 may also include a surface texture and/or an additional material to accomplish the purpose of increased gripping. The gripping feature 24 may also provide rigidity to the overall structure of the catheter adapter 12.

Figure 2:
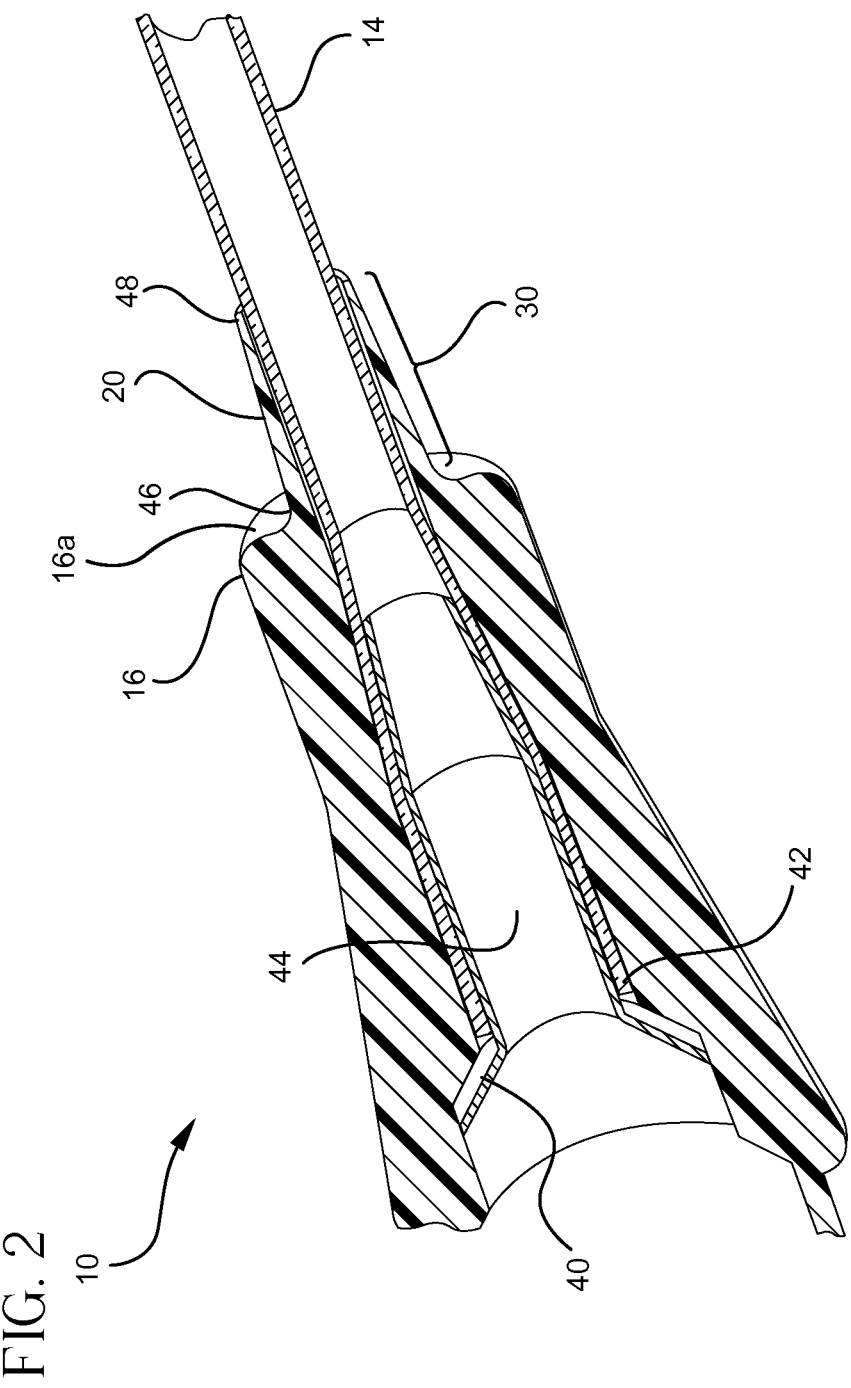
FIG. 2 is a cross section view of a catheter assembly showing the flexible extension support device in relation to attached catheter tube and catheter adapter first end.
Figure 3:
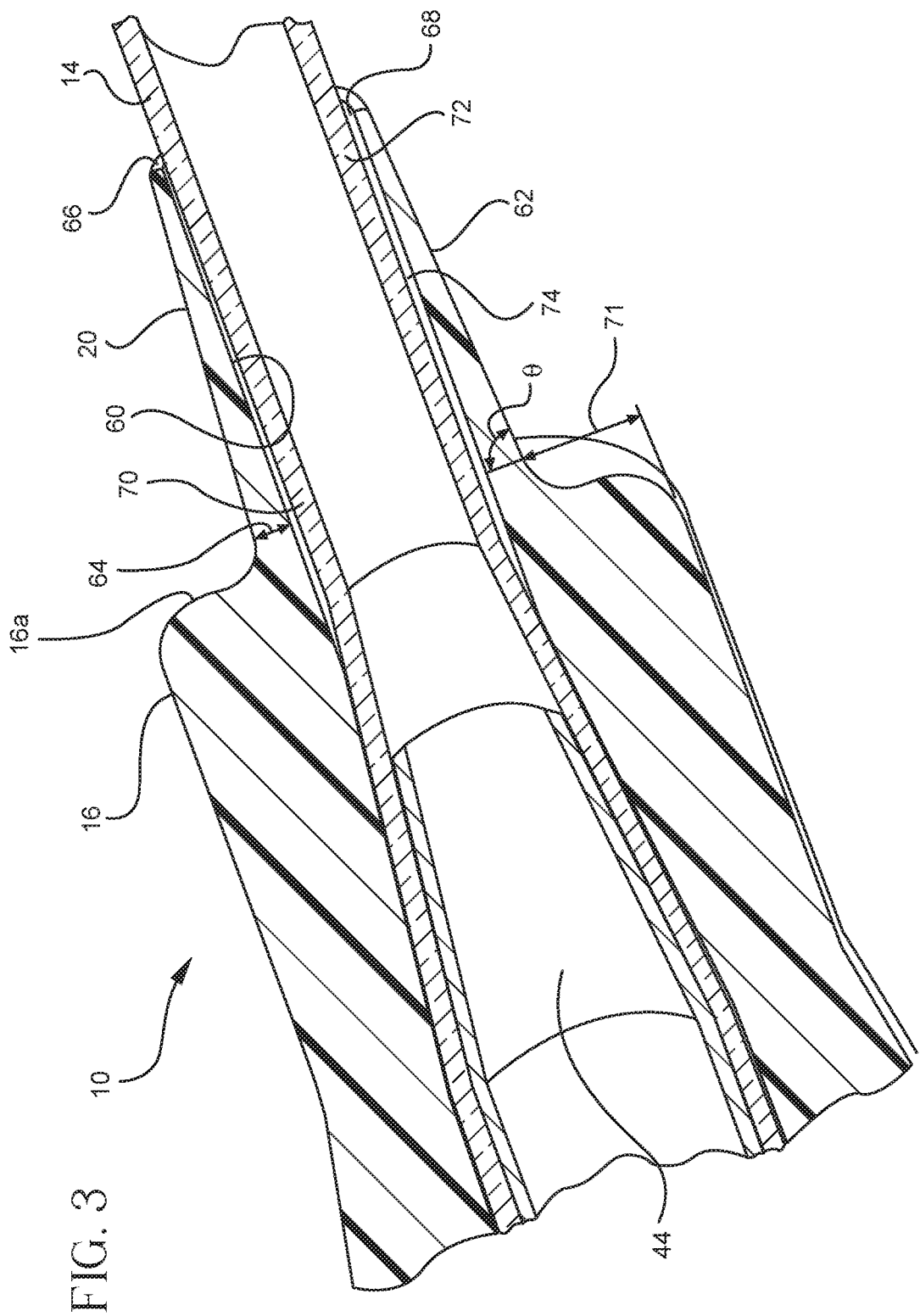
FIG. 3 is a cross section detail of flexible extension support device.

Referring now to FIGS. 2 and 3, the catheter tube 14 is mechanically attached to the catheter adapter 12 via insertion of a tubing insert 40 into the adapter end 42 of the catheter tube 14 whereby the tubing insert 40 secures the catheter tube 14 within the lumen 44 of the catheter adapter 12 in a fluidtight manner. The root region 30 of the catheter tube 14 is concealed inside the flexible extension 20 such that the flexible extension supports the catheter tube 14 root region 30 from undesirable occlusion. The flexible extension 20 is generally tubular as defined by an inner surface 60 and an outer surface 62 and a length. The length is defined as the distance between the proximal end 46 and the distal end 48 of the flexible extension 20. The outer diameter of distal surface 16a is greater than the outer diameter of outer surface 62 at the proximal end 48 of flexible extension 20. The flexible extension is radially centered on the distal surface 16a such that a step 71 is formed on distal surface 16a between the outer diameter of distal surface 16a and the outer surface 62 of the flexible member 20. The thickness of the flexible extension 20 tube wall varies along the length of the flexible extension 20 such that the flexible extension 20 is tapered along the length. For example, the proximal tube wall thickness 64 is greater than the distal tube wall thickness 66 where the tube wall thickness tapers from the proximal end 46 to the distal end 48 of the flexible extension 20.

The inner surface 60 of the flexible extension 20 approximates the outer profile 68 of the catheter tube 14 such that the inner surface 60 of the flexible extension 20 and the outer surface 74 of the catheter tube 14 are parallel. Additionally, an air gap 68 is provided between the outer surface 74 of the catheter tube 14 and the inner surface 60 of the flexible member 20 such that the root region 30 of the catheter tube 14 may move independently of the flexible extension 20. The tapering thickness of the flexible extension 20 tube wall is due to the outer surface 62 of the flexible extension 20 being ramped relative to the profile of the inner surface 60 of the flexible extension 20 wherein the height of the ramp decreases from the proximal end 46 to the distal end 48 of the flexible extension 20. This ramped outer surface 62 of the flexible extension 20 is accomplished by configuring the ramped angle θ at an angle of less than 90°.

The ramped outer surface 62 of the flexible extension 20 provides an inverse relationship between the thickness of the tube wall and the flexibility of the tube wall. For example, the proximal tube wall thickness 64 is greater than the distal tube wall thickness 66 however the flexibility of the proximal tube wall thickness 64 is less than the flexibility of the distal tube wall thickness 66. This inverse relationship along the length of the flexible extension 20 provides more flexibility, and therefore less support, for the distal end 72 of the root region. Additionally, this inverse relationship provides less flexibility, and therefore more support, for the proximal end 70 of the root region 30 where an occlusion is more likely to occur.

For example, the proximal end 70 of the root region 30 has greater potential for occlusion due to the proximity of the first end 16 of the catheter adapter 12. Therefore, without the flexible extension 20, the first end 16 of the catheter adapter 12 serves as a fulcrum over which the proximal end 70 of the root region 30 may bend upon movement of the catheter tube 14. The flexible extension 20 therefore provides less flexibility, and therefore more support to the proximal end 70 of the root region 30 where the proximal end 70 abuts the first end 16 of the catheter adapter 12 thereby minimizing the fulcrum effect of the first end 16 of the catheter adapter 12 on the proximal end 70 of the root region 30.

Additionally, an inverse relationship exists for the likelihood of occlusion where the likelihood of occlusion decreases as the distance to the first end 16 of the catheter adapter 12 increases. For example, where the proximal end 70 of the root region 30 is positioned close to the first end 16 of the catheter adapter 12, the likelihood of occlusion is great and therefore the flexible extension 20 must provide additional support to this end 70 of the root region 30. Conversely, where the distal end 72 of the root region 30 is positioned far from the first end 16 of the catheter adapter 12, the likelihood of occlusion is less and therefore the flexible extension 20 may provide minimal support to this end 72 of the root region 30. The inverse relationship regarding the likelihood of occlusion determines the tapering of the flexible extension 20, wherein the tapering is chosen such that the likelihood of occlusion is minimized for the entire root region 30 of the catheter tube 14.

Figure 4:
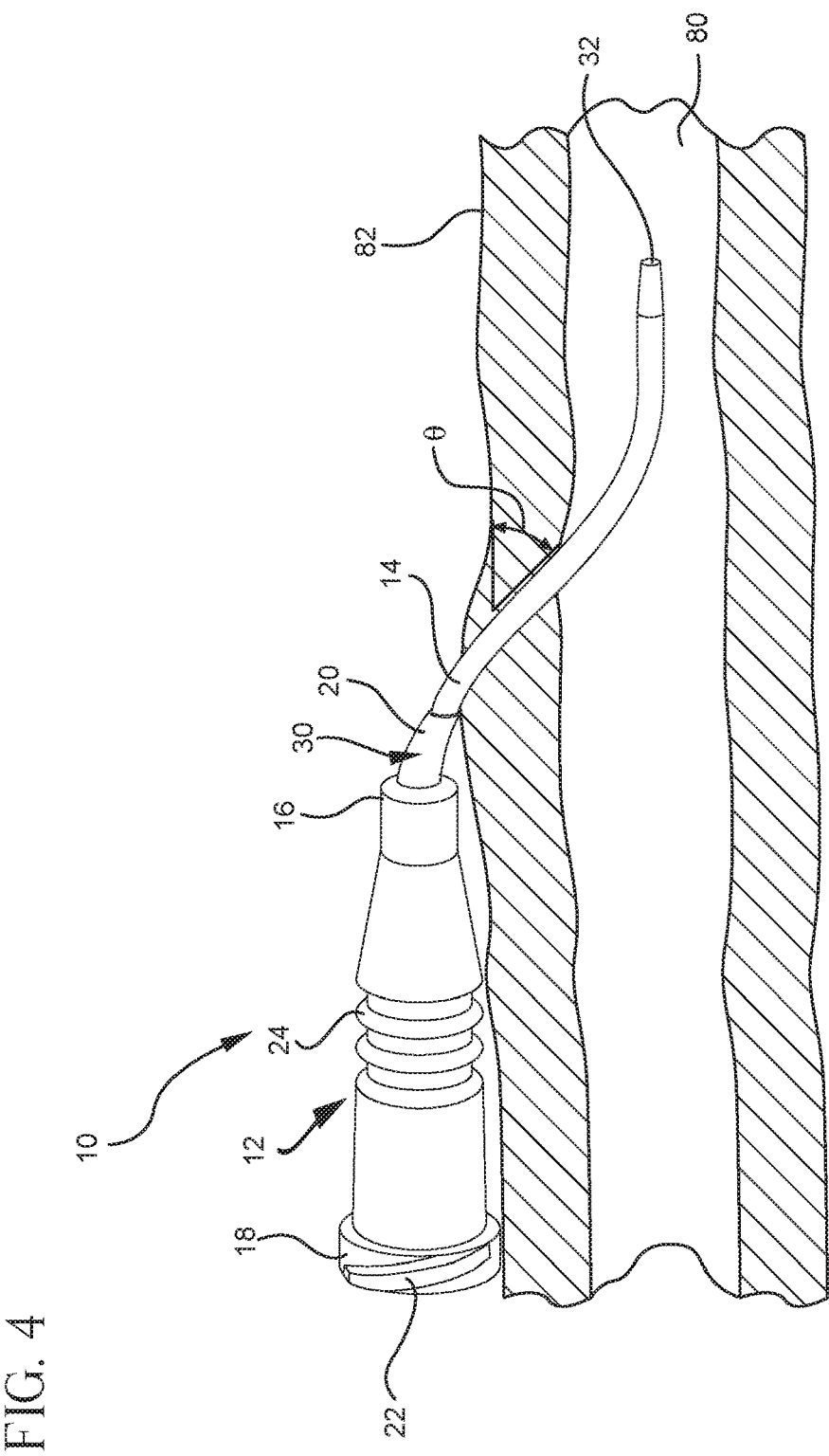
FIG. 4 is a partial perspective view of the catheter assembly following insertion of the catheter into a patient.

Referring now to FIG. 4, the catheter assembly 10 is illustrated showing the catheter tube 14 inserted into the vascular system 80 of a patient 82. The catheter tube 14 is inserted in a patient 82 such that the catheter tip 32 and the needle (not shown) enter the skin of the patient 82 at an angle θ' of about 30 degrees. Once the catheter tip 32 and the needle reach the interior of the vascular system 80, the catheter tube 14 is advanced into the vascular system 80 and the needle is removed from the catheter tube 14. As the needle is removed, the catheter tube 14 and catheter tip 32 remain in the vascular system 80 whereupon the catheter tube readjusts within the patient 82 such that the catheter tube 14 is positioned within the patient 82 at the degree of entry θ' and the catheter tip is generally parallel to the walls of the vascular system 80. Following removal of the needle, the catheter adapter 12 is secured to the patient 82 such that the catheter adapter 12 is generally parallel to the patient 82. In this position, the root region 30 of the catheter tube 14 arches to accomplish the transition of the catheter tube 14 from the catheter adapter 12 to the patient 82. Additionally, the flexible extension 20 is archedly biased by the arched root region 30, the arched flexible extension 20 thereby buttressing the arched root region 30 by adding support to the root region 30 thus preventing an occlusion of the catheter tube 14 at the root region 30.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An anti-occlusion catheter device comprising:
   a catheter adapter having a first, distal end, a second, proximal end, and a lumen that extends between the first and second ends, wherein the catheter adapter has a generally cylindrical shape, wherein the first end has a first outer diameter;
   a flexible extension that extends from a distal-most surface of the first end of the catheter adapter, wherein the flexible extension and the first end of the catheter adapter are constructed of a same material and are monolithically formed as a single piece, the flexible extension including an outer and an inner surface that extend from a proximal end of the flexible extension to a distal end of the flexible extension, the proximal end of the flexible extension being proximate the distal-most surface of the first end of the catheter adapter, a distance between the outer and inner surface being greater at the proximal end of the flexible extension than at the distal end of the flexible extension, the outer surface of the proximal end of the flexible extension having a second outer diameter that is less than the first outer diameter of the first end, the flexible extension being radially centered on the distal-most surface thereby forming a step between the distal-most surface and the flexible extension;
   an over-the-needle catheter tube for insertion into a patient, the catheter tube having a proximal end positioned within the lumen and a distal end that is positioned outside of the flexible extension such that a root region of the catheter tube is positioned within the flexible extension, the catheter tube being formed of a flexible material such that both the flexible extension and the root region of the catheter tube are flexible;

a tubing insert that is contained entirely within the catheter adapter and positioned within the lumen, the tubing insert having a distal end that inserts into the proximal end of the catheter tube to secure the catheter tube within the lumen in a fluidtight manner; and a hypodermic needle disposed within the catheter tube and configured to initially puncture skin of the patient to thereby insert the distal end of the catheter tube into the patient's vasculature and to then be retracted from the catheter tube through the proximal end of the catheter adapter, wherein a gauge of the hypodermic needle approximates an inner diameter of the catheter tube;

wherein the flexible extension is configured such that, after the distal end of the catheter tube is inserted into the patient's vasculature and the needle is withdrawn from the catheter tube, the flexibility of the flexible extension enables the flexible extension to arch to accommodate arching of the root region of the catheter tube that occurs as the catheter tube transitions from the catheter adapter to the patient's vasculature to thereby buttress the arched root region and prevent the arched root region from becoming occluded.

2. The catheter device of claim 1, wherein the flexible extension is molded as part of the catheter adapter.

3. The catheter device of claim 2, wherein the flexible extension is formed by allowing an amount of flash to extend beyond the first end in an injection mold.

4. The catheter device of claim 1, wherein the inner surface has a diameter that approximates an outer surface diameter of the catheter tube wherein the inner surface diameter is slightly greater than the outer surface diameter of the catheter tube such that an air gap is maintained between the two surfaces.

5. The catheter device of claim 1, wherein a Luer lock is positioned annularly on an outer surface of the second end.

6. The catheter device of claim 1, wherein the flexible extension prevents over insertion of the catheter tube.

7. The catheter device of claim 1, wherein the distal end of the tubing insert is positioned proximal to the proximal end of the flexible extension.

8. The catheter device of claim 1, wherein the lumen is tapered at the first, distal end and an outer diameter of the distal end of the tubing insert is also tapered to thereby cause the proximal end of the catheter tube to be secured between the tapered first, distal end of the lumen and the tapered distal end of the tubing insert.

9. The catheter device of claim 1, wherein the flexible extension is configured to arch approximately 30 degrees relative to a longitudinal axis of the catheter adapter.

10. The catheter device of claim 1, wherein the catheter adapter includes a gripping feature.

11. The catheter device of claim 1, wherein the first end of the catheter adapter is configured to function as a fulcrum over which a proximal end of the root region bends.

* * * * *